United States Patent
Yun et al.

(10) Patent No.: US 7,412,024 B1
(45) Date of Patent: Aug. 12, 2008

(54) X-RAY MAMMOGRAPHY

(75) Inventors: Wenbing Yun, Walnut Creek, CA (US); Yuxin Wang, Arlington Heights, IL (US)

(73) Assignee: Xradia, Inc., Concord, CA (US)

( * ) Notice: Subject to any disclaimer, the term of this patent is extended or adjusted under 35 U.S.C. 154(b) by 26 days.

(21) Appl. No.: 11/244,825

(22) Filed: Oct. 5, 2005

Related U.S. Application Data

(63) Continuation-in-part of application No. 10/990,198, filed on Nov. 16, 2004.

(60) Provisional application No. 60/616,177, filed on Oct. 5, 2004, provisional application No. 60/560,992, filed on Apr. 9, 2004.

(51) Int. Cl.
*G01N 23/087* (2006.01)
*G01T 1/20* (2006.01)
*H05G 1/64* (2006.01)

(52) U.S. Cl. .......... 378/37; 378/53; 378/98.3; 378/98.11; 378/98.12; 250/367; 250/368; 250/370.11

(58) Field of Classification Search .......... 378/37, 378/51, 53, 54, 98.3, 98.9, 98.11, 98.12; 250/367, 368, 370.11
See application file for complete search history.

(56) References Cited

U.S. PATENT DOCUMENTS

| 3,610,984 | A | * | 10/1971 | Seki et al. ............... 378/125 |
|---|---|---|---|---|
| 3,660,053 | A | | 5/1972 | Palme |
| 5,150,394 | A | | 9/1992 | Karellas |
| 5,235,191 | A | | 8/1993 | Miller |
| 5,375,158 | A | * | 12/1994 | Logan .................. 378/143 |
| 5,481,584 | A | | 1/1996 | Tang et al. |
| 5,497,008 | A | | 3/1996 | Kumakhov |
| 5,570,403 | A | | 10/1996 | Yamazaki et al. |
| 5,706,327 | A | * | 1/1998 | Adamkowski et al. ........ 378/37 |
| 5,712,890 | A | * | 1/1998 | Spivey et al. ............... 378/37 |
| 5,723,865 | A | | 3/1998 | Trissel et al. |
| 5,790,629 | A | | 8/1998 | Svensson et al. |
| 5,838,758 | A | * | 11/1998 | Krug et al. ............... 378/53 |
| 5,881,126 | A | * | 3/1999 | Momose ................. 378/36 |
| 6,018,564 | A | * | 1/2000 | Wilkins ................. 378/62 |
| 6,038,286 | A | | 3/2000 | Wagli et al. |
| 6,091,796 | A | | 7/2000 | Trissel et al. |
| 6,163,590 | A | * | 12/2000 | Wilkins ................. 378/43 |
| 6,226,353 | B1 | * | 5/2001 | Wilkins et al. ............. 378/98.9 |

(Continued)

OTHER PUBLICATIONS

Allman, B. E., et al., "Phase Radiography with Neutrons." Nature 408: 158-159, (2000).

(Continued)

*Primary Examiner*—Allen C. Ho
(74) *Attorney, Agent, or Firm*—Houston Eliseeva LLP

(57) ABSTRACT

A digital x-ray phase contrast soft tissue imaging and mammography system offers significant cancer detection sensitivity and a significant improvement in accurate detection and interpretation of mammograms. In addition, the proposed system produces digital mammograms and thus has the advantages of digital mammography. The system overcomes the limitation of the current approaches to mammography using phase contrast effects and offers substantially higher performance than the current mammography used in hospitals and clinics. The proposed system uses the phase contrast imaging, in a breast and other soft tissue structures, instead of absorption contrast employed in the current x-ray mammography, allowing detection of smaller disease structures with substantial reduction in radiation dose.

14 Claims, 1 Drawing Sheet

U.S. PATENT DOCUMENTS

| | | | |
|---|---|---|---|
| 6,285,740 | B1 | 9/2001 | Seely et al. |
| 6,353,657 | B1 | 3/2002 | Bayrock et al. |
| 6,356,617 | B1 | 3/2002 | Besch et al. |
| 6,470,068 | B2 | 10/2002 | Cheng |
| 6,584,170 | B2 | 6/2003 | Aust et al. |
| 6,934,409 | B2 * | 8/2005 | Ohara .................. 382/132 |
| 6,973,161 | B2 * | 12/2005 | Ohtsuki .................. 378/57 |
| 7,010,092 | B2 | 3/2006 | Winsor |
| 7,019,304 | B2 | 3/2006 | Albagli et al. |
| 7,027,556 | B2 * | 4/2006 | Ohara .................. 378/62 |
| 7,103,140 | B2 * | 9/2006 | Amitani et al. .......... 378/37 |
| 7,171,031 | B2 * | 1/2007 | Sakaida .................. 382/128 |

OTHER PUBLICATIONS

Barty, A., et al., "Quantitative Phase Tomography." Optics Communications 175: 329-336 (2000).

Chapman, D., et al., "Diffraction Enhanced X-ray Imaging," Phys. Med. Biol. 42, 2015 (1997).

Davis, T. J., et al., "Phase-contrast Imaging of Weakly Absorbing Materials Using Hard X-rays," Nature, 373, 595 (1995).

Nugent, K. A., et al., "Quantitative Phase Imaging Using Hard X-Rays," Physical Review Letters 77(14): 2961-2964 (1996).

Pisano, E.D., et al., "Human Breast Cancer Specimens: Diffraction-enhanced Imaging with Histologic Correlation—Improved Conspicuity of Lesion Detail Compared with Digital Radiography," Radiology 214, 895 (2000).

Snigirev, A., et al., "On the Possibilities of X-ray Phase Contrast Imaging by Coherent High Energy Synchrotron Radiation," Rev. Sci. Instrum. 66, 5486 (1995).

Wang, Y., "A High Throughput X-ray Microtomography System at the Advanced Photon Source," Review of Scientific Instruments 72(4): 20062-20068 (2001).

Wilkins, S. W., et al., "Phase-contrast Imaging Using Polychromatic Hard X-rays," Nature 384, 335 (1996).

Koch, Andreas, et al., "X-ray imaging with submicrometer resolution employing transparent luminescent screens," Journal of Optical Society of America, 15(7), Jul. 1998, abstract only.

* cited by examiner

X-RAY MAMMOGRAPHY

RELATED APPLICATIONS

This application claims the benefit under 35 USC 119(e) of U.S. Provisional Application No. 60/616,177, filed Oct. 5, 2004, which is incorporated herein by reference in its entirety.

This application is a Continuation-in-Part of U.S. application Ser. No. 10/990,198, filed Nov. 16, 2004, which claims the benefit under 35 USC 119(e) of U.S. Provisional Application No. 60/560,992, filed Apr. 9, 2004, both of which are incorporated herein by reference in their entirety.

BACKGROUND OF THE INVENTION

X-ray mammography is currently the primary method for breast cancer screening. Recent randomized clinical trials have shown that screening mammography has reduced mortality from breast cancer by 25-30% in women between the ages 50-70, and by 18% among between the ages of 40 and 50. A recent report by the Institute of Medicine has indicated much could be done to improve breast cancer screening and save even more lives. The report calls for technological improvement in the accurate interpretation of mammograms and the development of new screening technologies. With the best screening method currently available, mammograms still miss up to 17% of tumors and give about 10% false-positive result.

The current medical mammography systems use absorption contrast and the images are recorded on film. Significant improvement can be made in both the image formation mechanism and image recording, as substantial gains in imaging contrast and detector efficiency are possible with recent technological development.

SUMMARY OF THE INVENTION

The present invention concerns a digital phase contrast mammography. This new concept is characterized by true phase imaging of structures in a breast and thus offers significant cancer detection sensitivity and a significant improvement in accurate detection and interpretation of mammograms. In addition, the proposed system produces digital mammograms and thus has the advantages of digital mammography.

We propose a new digital phase contrast mammography technique that overcomes the limitation of the current approaches to mammography using phase contrast effects and offers substantially higher performance than the current mammography used in hospitals and clinics. The proposed system uses the phase contrast imaging, in a breast and other soft tissue structures by more than 100 times over the absorption contrast employed in the current x-ray mammography, allowing detection of smaller disease structures with substantial reduction in radiation dose. In fact, since the contrast mechanism does not depend on the x-ray radiation being absorbed by the patient, substantially higher energy x-ray radiation, for example 59.3 kilo electron Volt (keV) radiation from tungsten may be used to reduce the dosage to patient to by over an order of magnitude. Also, the system can obtain true phase images of all structures in a breast and other soft tissue structures and allow doctors to easily interpret the radiographs and identify cancerous tissues from benign and normal tissues, thus improving accuracy of diagnostics. Third, the system can produce digital mammograms that offer well-established advantages of digital mammography, such as a large dynamic range in recording various features and the use of image processing algorithms to potentially automate the tumor identification process during the initial screening. Finally, the proposed system can have a high throughput and may be built at a low cost, thus permitting wide practical deployment.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
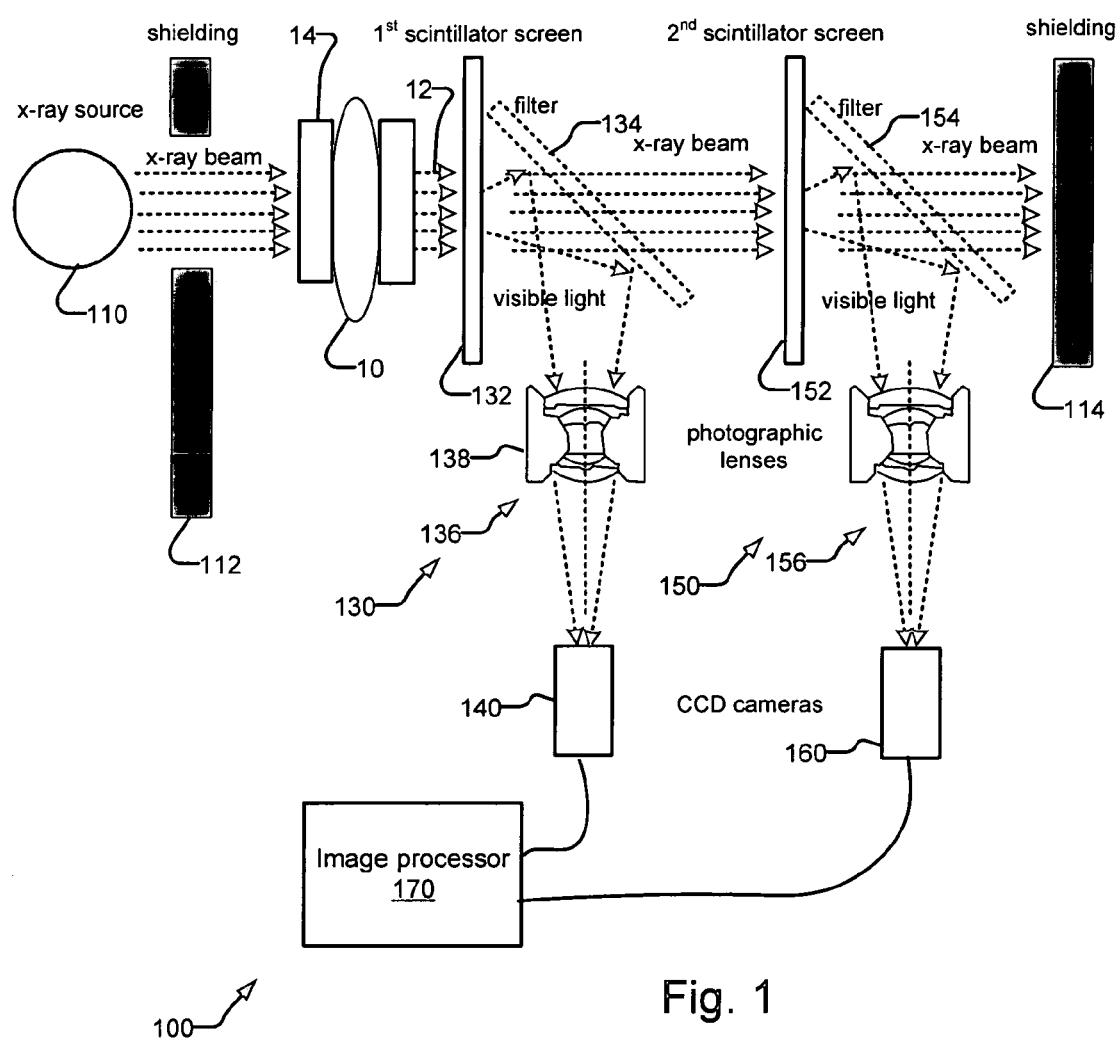
FIG. 1 is a side plan, schematic view of a phase contrast x-ray imaging system according to the present invention.

Phase contrast x-ray imaging is a recent approach that offers substantially enhanced image contrast over the absorption contrast used in medical x-ray radiography since the discovery of x-rays by Rontgen over a hundred years ago. The contrast enhancement is especially large for materials having low atomic number materials such as organic material/tissues including blood vessels, muscle and fatty tissues. As will be explained below, the contrast enhancement can be theoretically up to 1000 times greater and can be used to develop highly effective new x-ray diagnostic equipments for medical applications, such as imaging very early stages of tumor formation which typically has substantially smaller sizes while substantially reducing the radiation dose to the patients.

X-ray image formation results from modification of x-rays traveling through the object and the modification can be described using a complex index of refraction n. In the x-ray region, n is very close to unity and can be written as $n=1-\delta-i\beta$, where $\beta$ and $\delta$ describes the absorption and phase shift of x-rays, respectively. The phase shift term $\delta$ is directly related to magnitude of the refraction effect as in conventional optics. At typical mammography x-ray energy ~20 keV, $\delta$ is on the order of $10^{-7}$ and is about 1000 times bigger than $\beta(\sim 10^{-10})$. It is therefore more effective to perform x-ray imaging based on the phase shifting effect (referred to as phase contrast imaging) that offers substantially higher image sensitivity than the conventional radiography based on absorption contrast. An additional benefit of phase contrast imaging is that the phase contrast decreases linearly with increase in x-ray energy for biological samples while absorption contrast falls off substantially faster and decreases with the third power of x-ray energy. This makes it possible to use higher energy x-ray radiation to drastically reduce the dosage to be delivered to the patient during the exposure.

Current research is exploring ways to exploit the advantages of the large intrinsic phase contrast to either to increase resolution and image sensitivity or to reduce radiation dose. These approaches fall into three broadly categories.

Approaches in the first category detect the wave front distortion of the transmission x-ray beam introduced by the object to the incident x-ray beam. The wave front distortion is a result of spatial variation of the refractive index within the object that causes x-rays to be refracted from their propagation direction. The simplest form of this category is frequently referred to as in-line phase-contrast imaging technique and it uses a suitably collimated x-ray beam, either from a synchrotron source [A. Snigirev et al., Rev. Sci. Instrum. 66, 5486 (1995)] or a microfocus x-ray source [S. W. Wilkins et al., Nature 384, 335 (1996)], to illuminate the object. To detect the refraction effect due to the phase variation in the object (i.e., phase contrast), a position sensitive detector array is placed at a large distance behind the object as the refraction angle is proportional to $\delta$, which is very small. The optimal position of the detector for best enhancement effects varies from sample to sample depending on the x-ray energy and the size of the features of interest. It is important to point out that this technique generally does not image the true phase distribution within the object but obtains images resulting mostly from phase effects rather than absorption effects. This technique works very well for imaging objects containing a low density of structures. It is very challenging to apply this technique to objects containing a large number of overlapping structures due to the effects of multiple scattering within the object resulting in x-ray images that are hard to extract useful information, which is an ongoing computational and physics challenge. It is therefore difficult to apply this technique to mammography.

An improved form of the in-line phase contrast imaging technique in the first category, popularly referred to as diffraction enhanced imaging (DEI), uses perfect single crystals to improve both the collimation of the illumination beam and the sensitivity of detecting the wave front distortion of the transmission beam [see for example, T. J. Davis et al., Nature, 373, 595 (1995); D. Chapman et al., Phys. Med. Biol. 42, 2015 (1997); E. D. Pisano et al., Radiology 214, 895 (2000)]. The small angular acceptance of the crystals, ranging from $10^{-6}$ to $10^{-4}$ depending on the crystal reflection and the x-ray energy, is exploited to filter out x-rays outside the angular acceptance of the crystal placed in the illumination beam and in front of the object, and to analyze the angular spectrum of the transmission beam with a high angular resolution. DEI technique offers significant improvement over the in-line phase contrast imaging technique in terms of feature detection sensitivity resulting from the improvements in the angular filtering in the illumination beam and the detection sensitivity of the wave front distortion of the transmission beam. However, DEI technique has two major drawbacks: low efficient use of x-ray fluxes from the x-ray source due to the small angular acceptance and directionality of the angular collimation in the illumination beam and angular analysis in the transmission beam, which results in an image contrast dependence on the orientation of features with respect to the beam collimation direction. So far most EDI experiments have been carried out on synchrotron radiation facilities and demonstrated recently improved cancer detail visualization. The low brightness of laboratory x-ray sources may prevent practical use of this technique for clinical medical applications unless an x-ray source with significant higher brightness can be developed.

The second approach uses x-ray interferometer methods that were pioneered by Ulrich Bonse and Michael Hart [U. Bonse, M. Hart, Appl. Phys. Lett. 6, 155 (1965)]. The x-ray interferometer functions similar to a well-known Michaelson interferometer operating in the visible light spectrum and can be used to map the real phase distribution of an object, which is important for imaging complex structures like a breast. In recent years, x-ray interferometer has been incorporated into computed tomography and impressive 3-D images of biological specimens have been obtained using synchrotron x-ray source sources [A. Momose, Nucl. Instrum. Meth. A 362, 622 (1995); A. Momose et al., Nat. Med. 2, 473 (1996)]. However, the x-ray interferometer technique imposes very stringent requirements on the mechanical system, including scanning of an analyzer crystal with sub-nanometer precision and sub-nanoradiation angular stability between the crystals. The throughput is also limited due to the small angular acceptance imposed by the need of perfect crystals. As a result, its use for mammography with a laboratory source may not be practical.

The third approach is based on a recent developments by several groups (Nugent and Trebes 1993; Nugent 1996; Paganin 1998; Allman 2000; Barty 2000). The true phase information is obtained by first recording two or more images acquired at different distances from the object and then reconstructing the wave field using a phase retrieval algorithm based on the use the transport of intensity equation (TIE), first developed by Nugent (Nugent 1996).

The phase map of the sample is reconstructed using the TIE method. This will enhance the contrast of organic features to the level that is higher than the metallic or hard tissue features. It is important to point out that the reconstructed phase map is the linear sum of the phase shifts through the sample, therefore they can be used directly with parallel-projection tomography algorithms to reconstruct the 3D image of the subject as in traditional CT scans.

This method is based on the knowledge that the intensity and the phase of a propagating wave are coupled in a unique manner, and knowledge of one can be used to determine the other. A good physical example is the water in a swimming pool. The waves on the surface of the pool absorb little light, but cause significant phase shift. The intensity pattern at the bottom of the pool is the result of the intensity change due to the wave propagation through water.

For a time-invariant and coherent wave the intensity distribution of the wave I and the gradient of its phase $\phi$ are related by:

$$\nabla \cdot [I(\vec{r})\nabla \phi(\vec{r})] = 0,$$

For paraxial beam conditions, this equation leads to the transport of intensity equation $$\frac{\partial I(\vec{r})}{\partial z} = \nabla_\perp \cdot [I(\vec{r})\nabla_\perp \phi(\vec{r})],$$

where z is the beam axis and $\nabla_\perp$ is the 2D gradient operator in the plane perpendicular to the beam axis. By acquiring two images at different z positions, we can obtain the two images with value of I. These two images can be used to compute the value of $\phi$, which represents the values of integrated relative phase shift through the sample. Using again the swimming pool example, it is similar, in principle, to reconstructing the surface wave pattern by measuring the intensity pattern at two depths.

We propose a new mammography concept that overcomes some key limitations of the phase contrast imaging approaches described in the previous section. This new concept is characterized by true quantitative phase imaging of structures in a breast and other soft tissue and a high throughput with a low cost x-ray source that may allow practical clinical applications. The proposed system improves upon current film-based radiography systems in both the image formation mechanism and image recording to gain substantial imaging contrast and detector efficiency. Both translate into drastically increased detection sensitivity and as the same time reduced radiation dosage to the patient.

Typical phase-contrast imaging with a projection-type microscope requires two exposures with the detector placed at different distances from the sample. Motion-induced differences in the subject during the two exposures often causes artifacts in the reconstructed phase image and limits the image resolution to tens of um. The proposed instrument, however, uses a unique phase-contrast imaging scheme that performs phase-contrast imaging with a single exposure. In this scheme, the detector comprises two scintillators separated by a filter that reflects the visible light generated by the first scintillator screen to the first detector, and allows the x-ray beam to pass and reach the second scintillator and associated detector system, of which the scintillator located at a predetermined distance from the first scintillator. Therefore the two images are acquired in a single exposure and the phase information of the object can be deduced from the propagation property of the imaging forming x-rays between the two scintillators using a well-established method. This scheme also resolves the contradictory requirement of high resolution and high efficiency image recording of high energy x-rays: the former typically requires a thinner scintillator while the later requires a thicker scintillator. Therefore, the proposed scheme increases the overall detection efficiency and reduces the dosage to the sample.

One detector system that is applicable to the inventive system is disclosed in U.S. patent application Ser. No. 10/990, 198, filed on Nov. 16, 2004, by Yun, et al. entitled "Dual-Band Detector System for X-Ray Imaging of Biological Samples", which is incorporated herein in its entirety by this reference.

Optimal x-ray energy for mammography should have sufficient transmission through a breast compressed between two plates in a medical mammography machine and adequate image contrast. In general, the transmission increases with the third power of x-ray energy while the image contrast on x-ray energy depends strongly on what type of image contrast is employed. Absorption contrast, which is used in the existing medical mammography machines, decreases with the third power of x-ray energy while the proposed phase contrast decreases only linearly with x-ray energy. Therefore, the present digital phase contrast mammography system can use higher energy x-rays than that used in the existing mammography machines which typically uses 17.5 keV x-rays (Mo Target). In one embodiment, 22.2 keV x-rays (Ag target) are used. In comparison, with a breast compressed to 2 centimeters (cm) thickness, approximately 70% of 17.5 keV radiation is absorbed by the patient while about 50% absorption is expected with 22.2 keV radiation, but with about a factor of 1000 times increase in image contrast for soft tissues. Since the phase contrast mechanism does not depend on the absorption of the x-ray radiation, much higher x-ray energy can be used. For example an x-ray source with tungsten (W) target can be used to generate 59.3 keV radiation. At this energy a 2-cm thick compressed breast absorbs only about 10% of the radiation, while still gaining over two orders of magnitudes in contrast over current absorption-contrast systems using 17.5 keV x-rays.

Other important factors must be considered for selecting the optimal x-ray energy including the achievable detector efficiency and resolution and available x-ray source. A scintillated charge-coupled device (CCD) detector coupled with a microscope objective currently provides the highest resolution among electronic detectors. X-rays with higher energy generally have a longer penetration depth, hence a longer path for the fluorescent emission. This path length may be too long to be efficiently collected by a high numerical aperture (NA) objective since a large NA results in a shallower depth of field. Therefore, x-rays with lower energies are favorable to achieve high resolution. Two commonly used anode materials provide emission lines above 15 keV: Mo at 17.4 keV and W at 59.3 keV. It is generally easier to develop high resolution detectors for lower energy x-ray.

As an x-ray wave passes through an object it under goes absorption and phase shift as described by:

$$\phi(z) = \phi(0)e^{iknz},$$

where k is the wave number and n is the complex index of refraction defined as:

$$n = 1 - \delta - i\beta.$$

The value of $\delta$ characterizes the phase shift and $\beta$ characterize the absorption. The attenuation length is $$\mu = \frac{\lambda}{4\pi\beta},$$

and the length to produce a $2\pi$ phase shift is:

$$z_{2\pi} = \frac{\lambda}{1 - \delta}.$$

The values of $\delta$ and $\beta$ for protein and water at 17.4 keV are:

| | | |
|---|---|---|
| water: | $\delta = 7.58 \times 10^{-7}$ | $\beta = 4.63 \times 10^{-10}$ |
| protein: | $\delta = 9.83 \times 10^{-7}$ | $\beta = 5.32 \times 10^{-10}$ |

The intrinsic phase contrast between protein and water is about 12% for a thickness of about 20 micrometers (μm). Actual contrast manifested in the images will be somewhat less. The number of photons required to image the protein features is given by:

$$N = \frac{SNR^2}{TC^2},$$

where SNR is the signal-to-noise ratio, T is the transmission, and C is the contrast. It is generally accepted that features can be identified with a signal-to-noise level of 5:1. In this case, about 6000 photons are required for each exposure. Then each 10 μm pixel volume absorbs about 3 photons. These photons deposit $8 \times 10^{-15}$ J of energy into a volume of $10^{-12}$ kg of mass. The resulting dosage is 8 mGray, or 0.8 rem. A tomographic data set with 60 projections can be acquired with less than 50 rem dosage. It is clear that a single exposure will have a negligible adverse effect on the subject. When imaging at 2 μm resolution, however, the dosage will increase by a factor of 1000 to about 800 rem. This level of radiation will likely kill the subject, and is therefore appropriate only for terminal studies or non-live samples.

The absorption contrast for which is significantly lower than phase contrast and have a low contrast can only image bone structures. Soft tissues can be imaged only with the use of contrast enhancing agents. They typically have a resolution of 20 μm. These systems are generally not well suited for imaging soft tissue and organs, which are better imaged in phase contrast. A few phase contrast systems are also available. They typically acquire two images at different distances from the sample. The integrated phase shift through the sample can then be extracted by examining the phase propagation of the x-ray beam between the two positions. These systems are able to image soft tissue structures of a sample without the use of contrast agents. The need to acquire two images at different times, however, poses difficulties with a live sample that will unlikely remain still between the two exposures. Therefore the subject typically needs to be sedated during imaging. To date, 3D tomographic imaging capabilities are commercially available only with absorption-contrast instruments.

The instrumentation setup of the low-resolution mode is shown in FIG. 1. An Ag x-ray source 110 generates 22.17 keV x-rays. The x-rays will pass through the object 10, has as an animal, breast or object including soft tissue, to reach the first detector 130. In the illustrated example, this biological sample is held in a sample holder 14. In the example of a mammography system, this sample holder 14 is often a clamping system for holding the breast. In other example, the holder secures and positions the sample 10 in the beam 12.

If the subject is sufficiently far away from the first scintillator 132, the x-ray beam 12 can propagate enough distance to produce an image dominated by phase contrast. A filter 134 is placed behind the first scintillator 132 to reflect the visible light or first optical signal generated at the scintillator 132 to the optical stage 136 of detector 130 and allow the x-ray beam to pass through. The filter 134 can be constructed from a pellicle membrane or a silicon wafer with about 70 μm thickness. The scintillator 132 will be a single crystal scintillator, for example made from $CdWO_4$. A phosphor screen scintillator is inappropriate because the grain will modify the phase of the x-ray beam.

The first optical stage 136 preferably comprises anoptical imaging lens system 138, such as a photographic lens system, for imaging the optical signal from the first scintillator 132 onto a first optical detector, such as a CCD detection camera 140.

The x-ray beam passing through the first filter 134 then reaches the second scintillator 152 of the second detector 150 to generate an image with further wave propagation information. The generated second optical signal is reflected by fold mirror 154 to a second lens system 138 of the optical stage 156. The image is then detected by a second optical detector/camera 160.

Utilizing the transport of intensity equations the phase characteristics of beam 12 are be recovered by image processor 170 using the image information of the first and second cameras 140,160. In this way a phase-contrast image derived with a single exposure. It is therefore superior to the traditional method of making two exposures with a single detector at different positions when imaging live subjects.

In one embodiment, the source 110 is a microfocus x-ray source optimized for brightness, such as those supplied by either Oxford Instruments or Hamamatsu. Such a source has a nominal spot size of 5-10 μm and input power of 10 W. It generates a brightness of approximately $10^{11}$ photon/(sec. $mm^2$ $mrad^2$).

The first scintillator 132 will be between 3 and 10 μm thick, preferably a 6 μm thick $CdWO_4$ crystal. The scintillator 132 is preferably bonded to a microscope cover-glass with a thickness of 170 μm and polished to a 6 μm thickness. This scintillator will absorb about 25% of the incoming radiation. The transmission of the glass substrate is about 85%.

After passing through the first scintillator 132, the visible light emitted by the scintillator and the x-ray beam will reach the silicon filter 134 angled at 45° which will reflect 95% of the visible light towards the detector's optical stage 136 and transmits 85% of the x-ray. The visible light will be imaged to the CCD camera 140 by a photographic lens system 138. With the use of a high-quality photographic lens, a resolution of 5 μm can be achieved on the scintillator 132.

The x-ray beam will reach the second scintillator 152 and filter assembly. The second scintillator 152 preferably has a thickness of about 10-20 μm, preferably about 15 μm, which absorbs about 52% of the incoming radiation. After counting the transmission through the first scintillator 132 and filter 134, the second scintillator 152 absorbs about 25% of radiation passing through the sample 10, and therefore produces a similar signal level as the first detector. After passing through the second scintillator 152 and filter 154, the direct radiation will be absorbed by radiation shielding 114. Source shielding 112 is also preferably used to minimize ancillary exposure of subject and others.

The use of a thinned scintillator has the benefit of absorbing very little high energy radiation generated by the x-ray source, therefore making the detected radiation nearly monochromatic. By angling the visible light path 90° from the x-ray path, the high energy spectrum is not able to directly reach the cameras 140, 160, thereby reducing the background signal.

To achieve the required resolution, we will place the sample 10 between 0.1 and 1 meter, preferably about 275 mm, away from the x-ray source 110 and the first scintillator 132 is about 0.01 to 0.1 meters, or about 50 mm, from the sample 10. The second scintillator 152 is placed 0.01 to 0.1 meters, or about 50 mm, away from the first scintillator 132. With this geometry, about 65,000 photons can be expected per 20 um resolution element per second. Therefore, to achieve the 5,000 photons per exposure, an exposure time of 100 milliseconds is needed. A few minutes will be required to acquire a tomographic data set with 60 projections.

Since the x-rays passing through the first scintillator 132 need to propagate to the second scintillator 152, the first scintillator 132 and the first filter 134 must not introduce excessive phase distortion to the x-ray wave 12. Therefore the scintillator, its substrate, and the filter must be made from uniform materials that have parallel surface with good flatness. The preferred scintillator material is $CdWO_4$ on glass substrate. There are two methods of fabricating the scintillator. In one example, epitaxial growth methods are used to deposit $CdWO_4$ crystal on a standard microscope cover-glass with 170 μm thickness. Alternatively, the polishing techniques are used to fabricate the scintillator: a bulk $CdWO_4$ crystal will be bonded to a cover-glass substrate and then polished to the required thickness with a lapping and polishing machine. An optical quality surface can be achieved with both methods. We will use a thin silicon wafer as the filter. Highly polished silicon wafers of the required thickness are commercially available. Photographic lenses with high resolution can also be obtained commercially. The x-ray source and the detector system will be integrated with motion systems to realize the digital mammography system 100.

The image processor 170 executes a software algorithm based on the transport of intensity equation (TIE). Software for this application can be licensed from IATIA, Inc., which was established in 2000 to commercialize this algorithm to optical, electron, and x-ray microscopes. The algorithm is used for phase reconstruction and optimized for the digital mammography applications.

While this invention has been particularly shown and described with references to preferred embodiments thereof, it will be understood by those skilled in the art that various changes in form and details may be made therein without departing from the scope of the invention encompassed by the appended claims.

What is claimed is:

1. A phase contrast x-ray imaging system, comprising:
   a sample holder comprising a clamping mechanism for holding a breast;
   an x-ray source for generating an x-ray beam for irradiating the sample;
   a first detector for generating a first image of the breast from the x-ray beam, wherein the first detector comprises a first scintillator for converting the x-ray beam into a first optical signal, a first optical detector for detecting the first optical signal, and a first mirror for directing the first optical signal out of a path of the x-ray beam to the first optical detector;
   a second detector for generating a second image of the breast from the x-ray beam, wherein the second detector comprises a second scintillator for converting the x-ray beam into a second optical signal, a second optical detector for detecting the second optical signal, and a second mirror for directing the second optical signal out of a path of the x ray beam to the second optical detector; and
   an image processor for combining information from the first image and the second image to generate a phase contrast image of the breast.

2. A system as claimed in claim 1, wherein the first detector and the second detector are at different distances from the sample holder.

3. A system as claimed in claim 1, wherein the x-ray source is an electron bombardment x-ray source.

4. A system as claimed in claim 3, wherein a target of the source is silver.

5. A system as claimed in claim 3, wherein a target of the source is tungsten.

6. A system as claimed in claim 1, wherein the x-ray beam comprises radiation having an energy of greater than 7.5 keV.

7. A phase contrast x-ray imaging system, comprising:
   a sample holder for holding a biological sample;
   an x-ray source for generating an x-ray beam for irradiating the sample;
   a first detector for generating a first image of the biological sample from the x ray beam, wherein the first detector comprises a first scintillator for converting the x-ray beam into a first optical signal, a first optical detector for detecting the first optical signal, and a first mirror for directing the first optical signal out of a path of the x-ray beam to the first optical detector;
   a second detector for generating a second image of the biological sample from the x-ray beam, wherein the second detector comprises a second scintillator for converting the x-ray beam into a second optical signal, a second optical detector for detecting the second optical signal, and a second mirror for directing the second optical signal out of a path of the x ray beam to the second optical detector; and
   an image processor for combining information from the first image and the second image to generate a phase contrast image of the sample;
   wherein the image processor combines information from the first image and the second image to generate a phase contrast image using the transport of intensity equation technique.

8. A system as claimed in claim 7, wherein the sample holder is a mechanism for holding a breast.

9. A system as claimed in claim 7, wherein the sample holder is a clamping mechanism for holding a breast.

10. A system as claimed in claim 7, wherein the x-ray source is an electron bombardment x-ray source.

11. A system as claimed in claim 10, wherein a target of the source is silver.

12. A system as claimed in claim 11, wherein the sample holder is a mechanism for holding a breast.

13. A system as claimed in claim 10, wherein a target of the source is tungsten.

14. A system as claimed in claim 13, wherein the sample holder is a mechanism for holding a breast.

* * * * *